(12) United States Patent
Herceg

(10) Patent No.: US 11,349,343 B2
(45) Date of Patent: May 31, 2022

(54) METHOD AND APPARATUS FOR ESTIMATING A MEASURED PARAMETER

(71) Applicant: Nokia Technologies Oy, Espoo (FI)

(72) Inventor: Marijan Herceg, Osijek (HR)

(73) Assignee: NOKIA TECHNOLOGIES OY, Espoo (FI)

(*) Notice: Subject to any disclaimer, the term of this patent is extended or adjusted under 35 U.S.C. 154(b) by 0 days.

(21) Appl. No.: 17/163,142

(22) Filed: Jan. 29, 2021

(65) Prior Publication Data

US 2021/0249905 A1 Aug. 12, 2021

(30) Foreign Application Priority Data

Feb. 6, 2020 (EP) ..................... 20155758

(51) Int. Cl.
| | |
|---|---|
| *H02J 50/12* | (2016.01) |
| *A61B 5/1468* | (2006.01) |
| *H03K 5/24* | (2006.01) |
| *A61B 5/145* | (2006.01) |
| *A61B 5/00* | (2006.01) |
| *G08C 17/04* | (2006.01) |

(52) U.S. Cl.
CPC ............ *H02J 50/12* (2016.02); *A61B 5/1468* (2013.01); *H03K 5/24* (2013.01); *A61B 5/14532* (2013.01); *A61B 5/14539* (2013.01); *A61B 5/14542* (2013.01); *A61B 5/14546* (2013.01); *A61B 5/6802* (2013.01); *A61B 5/686* (2013.01); *G08C 17/04* (2013.01)

(58) Field of Classification Search
CPC .................................................. A61B 5/1468

USPC .......................................................... 307/104
See application file for complete search history.

(56) References Cited

U.S. PATENT DOCUMENTS

| | | | |
|---|---|---|---|
| 5,455,466 A | 10/1995 | Parks et al. | |
| 2017/0118543 A1* | 4/2017 | Ha .................. | H04B 5/0075 |
| 2019/0349652 A1 | 11/2019 | Greenewald et al. | |

FOREIGN PATENT DOCUMENTS

| | | |
|---|---|---|
| CN | 107659001 A | 2/2018 |
| CN | 109638937 A | 4/2019 |

(Continued)

OTHER PUBLICATIONS

Mandal et al., "Power-Efficient Impedance-Modulation Wireless Data Links for Biomedical Implants", IEEE Transactions on Biomedical Circuits and Systems, vol. 2, No. 4, Dec. 2008, pp. 301-315.

(Continued)

*Primary Examiner* — Joseph Chang
(74) *Attorney, Agent, or Firm* — Alston & Bird LLP

(57) ABSTRACT

A method and apparatus are provided to facilitate the estimation of a measured parameter. In the context of a method, a series of measurement and transmission phases are conducted. During the measurement phase, the method includes receiving an input based on a measured parameter and comparing a voltage that is based on the input that is received over time to a threshold. The method also includes triggering the transmission phase in which a control signal is provided to facilitate discharge of the voltage in response to satisfaction of the threshold. The method further includes evaluating the transmission phases to determine an estimate of the input that is based on the measured parameter. A corresponding apparatus is also provided.

20 Claims, 11 Drawing Sheets

(56) References Cited

FOREIGN PATENT DOCUMENTS

| EP | 1609501 A1 | 12/2005 |
|---|---|---|
| EP | 3134953 A1 | 3/2017 |
| JP | 2011-078512 | 4/2011 |
| WO | 2015/130902 A1 | 9/2015 |

OTHER PUBLICATIONS

Valente et al., "1.2V Energy-Efficient Wireless CMOS Potentiostat for Amperometric Measurements", IEEE Transactions on Circuits and Systems II: Express Briefs, vol. 67, No. 10, Oct. 2020, pp. 1700-1704.

Zuo et al., "A Low-Power 1-V Potentiostat for Glucose Sensors", IEEE Transactions on Circuits and Systems II: Express Briefs, vol. 62, No. 2, Feb. 2015, pp. 204-208.

Ha et al., "Energy Recycling Telemetry IC With Simultaneous 11.5 mW Power and 6.78 Mb/s Backward Data Delivery Over a Single 13.56 MHz Inductive Link", IEEE Journal of Solid-State Circuits, vol. 51, No. 11, Nov. 2016, pp. 2664-2678.

Liao et al., "A 3-µW CMOS Glucose Sensor for Wireless Contact-Lens Tear Glucose Monitoring", IEEE Journal of Solid-State Circuits, vol. 47, No. 1, Jan. 2012, pp. 335-344.

Li et al., "A Power and Data Decoupled Transmission Method for Wireless Power Transfer Systems via a Shared Inductive Link", Energies, vol. 11, No. 8, 2018, pp. 1-14.

Ali et al., "Inductive Link Design for Medical Implants", IEEE Symposium on Industrial Electronics & Applications, Oct. 4-6, 2019, pp. 694-699.

Extended European Search Report received for corresponding European Patent Application No. 20155758.4, dated Sep. 1, 2020, 10 pages.

Jiang et al., "An Integrated Passive Phase-Shift Keying Modulator for Biomedical Implants With Power Telemetry Over a Single Inductive Link", IEEE Transactions on Biomedical Circuits and Systems, vol. 11, No. 1, Feb. 2017, pp. 64-77.

Ha et al., "Energy-Recycling Integrated 6.78-Mbps Data 6.3-mW Power Telemetry over a Single 13.56-MHz Inductive Link", Symposium on VLSI Circuits Digest of Technical Papers, Jun. 10-13, 2014, 2 pages.

Oh, "A Low Power Integrated Circuit for Implantable Biosensor Incorporating an On-Chip FSK Modulator", Thesis, May 2008, 111 pages.

Office Action for Japanese Application No. 2021-016607 dated Jan. 5, 2022, 5 pages.

* cited by examiner

METHOD AND APPARATUS FOR ESTIMATING A MEASURED PARAMETER

TECHNOLOGICAL FIELD

An example embodiment relates generally to the measurement of a parameter and, more particularly, to a method and apparatus for estimating a measured parameter, such as a parameter measured by a sensor, e.g., a biosensor.

BACKGROUND

A variety of devices are utilized to measure various parameters of a subject, such as a person, an animal or the like. For example, various devices may be implanted in or worn by a subject with the device including one or more sensors configured to measure respective parameters of the subject. By way of example, biosensors may be utilized to measure various biosignals. In one example, amperometric electrochemical biosensors are utilized as complementary metal oxide semiconductor (CMOS) compatible devices for the measurement of biosignals, such as glucose levels, lactate levels, oxygen levels, pH levels, etc. Amperometric electrochemical biosensors convert the biosignals to a current having a value representative of the biosignals, such as the magnitude of the biosignals. In this regard, amperometric electrochemical biosensors include readout electronics, such as potentiostats, to control the potential difference inside electrode cells so as to transform the sensor signals to a corresponding current. Based on the current, a measure of the biosignals is obtained that provides information regarding the particular parameter of the subject that is being measured.

Although the devices utilized for the measurement of biosignals may be battery powered, such as in the form of a wearable smart device or other medical device, many of the devices, such as the devices implanted in a subject, do not include a battery and are, instead, wirelessly powered. These wirelessly powered devices generally include a primary circuit external to the subject and a secondary circuit worn by or implanted within the subject. The primary and secondary circuits may be inductively coupled such that the primary circuit can wirelessly provide power to the secondary circuit and the secondary circuit can wirelessly transfer data indicative of the measured parameter to the primary circuit for further processing and evaluation.

The primary circuit typically includes a power source and a resonant circuit formed of a serially connected inductor and capacitor. In this example, the secondary circuit also includes a resonant circuit including a parallel arrangement of an inductor and a capacitor. The resonant circuit of the secondary circuit is also generally disposed in parallel with a rectifier for converting the alternating current (AC) waveform provided by the inductive coupling to the primary circuit to direct current (DC), which is consumed by the load of the secondary circuit.

In order to transfer data from the secondary circuit to the primary circuit, such as data representative of the measured parameter, load shift keying (LSK) is often utilized. In LSK, data is transferred from the secondary circuit to the primary circuit while the resonant circuit of the secondary circuit is short circuited. However, while the resonant circuit of the secondary circuit is short circuited, the secondary circuit is unable to receive energy from the primary circuit since the input to the rectifier is short circuited.

The impact of short circuiting the resonant circuit of the secondary circuit is depicted in FIG. 1. In this regard, FIG. 1 depicts the voltage across the resonant circuit of the secondary circuit over the course of time. For much of time during the measurement of the parameter of interest, the resonant circuit of the secondary circuit has an AC waveform with a constant amplitude that is representative of the AC power being transferred from the primary circuit via its inductive coupling with the secondary circuit. During the transmission of data, such as data representative of the measured parameter, the resonant circuit of the secondary circuit is short circuited such that the voltage across the resonant circuit of the secondary circuit is zero as designated 10 in FIG. 1. Thereafter, even after the resonant circuit of the secondary circuit is no longer short circuited and the measurement of the parameter has recommenced, the secondary circuit experiences a transient phase 12 in which the amplitude of the AC voltage across the resonant circuit of the secondary circuit gradually increases from zero when the resonant circuit was short circuited, to the maximum amplitude of the AC waveform. As represented by the transient phase in the example of FIG. 1, even when the resonant circuit of the secondary circuit is no longer short circuited, the voltage across the resonant circuit of the secondary circuit does not have a maximum amplitude for a number of cycles, thereby correspondingly reducing the energy delivered to the rectifier and available to the load of the secondary circuit.

FIG. 1 depicts an example in which data is transferred from the secondary circuit to the primary circuit every ten clock cycles as designated 14 with the transient phase 12 limiting the power transfer for several of the cycles following the transmission phase. In instances in which the data transfer occurs more frequently, such as every three clock cycles, every five clock cycles, every eight clock cycles or the like, the negative impact of the transient phase on the transfer of power from the primary circuit to the secondary circuit and the corresponding reduction in power available to be rectified by the secondary circuit is even more notable with the transient phase negatively impacting the power transferred for a greater percentage of the clock cycles following the transmission phase.

BRIEF SUMMARY

A method and apparatus are therefore provided to facilitate the estimation of a measured parameter. In an embodiment that includes both a primary circuit and a secondary circuit that are inductively coupled, the method and apparatus of an example embodiment provide for data transfer, such a data representative of the measured parameter, without short circuiting the resonant circuit of the secondary circuit. Thus, energy may continue to be provided by the primary circuit to the secondary circuit and, in turn, to a rectifier of the secondary circuit not only during the measurement phase in which the parameter is being measured, but also during the transmission phase in which data is transferred from the secondary circuit to the primary circuit. Thus, the secondary circuit receives more consistent power and, as the result, operates more efficiently in terms of power transfer and utilization, while also providing for reliable data transfer and the accurate estimation of the measured parameter.

In an example embodiment, a method is disclosed that includes providing a series of measurement and transmission phases. During the measurement phase, the method further includes receiving an input based on a measured parameter and comparing a voltage that is based on the input that is received over time to a threshold. The method also includes triggering the transmission phase in which a control signal is provided to facilitate discharge of the voltage in response to satisfaction of the threshold. The method further includes evaluating the transmission phases to determine an estimate of the input that is based on the measured parameter.

The method of an example embodiment also includes inductively coupling to a primary circuit and receiving energy from the inductively coupled primary circuit during both the measurement and transmission phases. In this example embodiment, the method receives energy with a resonant circuit during the measurement phase. The resonant circuit includes an inductor configured to be inductively coupled to the primary circuit and a first capacitor disposed in parallel with the inductor. The method of this example embodiment may also include storing the voltage that is based on the input that has been received with a second capacitor during the measurement phase and switchably replacing the first capacitor with the second capacitor during the transmission phase such that the second capacitor is disposed in parallel with the inductor during the transmission phase. The estimate of the input that is based on the measured parameter may also be based upon the threshold and a capacitance of the second capacitor. In relation to receiving energy from the inductively coupled primary circuit, the method of an example embodiment receives energy in accordance with a resonant frequency. In this example embodiment, the control signal is provided for a single period as defined by the resonant frequency prior to returning to the measurement phase.

The method of an example embodiment receives the input by receiving current representative of the measured parameter. In this example embodiment, the method may also include measuring the parameter with a sensor that provides the current representative of the measured parameter and switchably disconnecting the sensor in response to the control signal to prevent receipt of the current representative of the measured parameter during the transmission phase. The method of an example embodiment evaluates the transmission phases to determine the estimate of the input by determining the estimate of the input based upon a time between transmission phases.

In another example embodiment, an apparatus is provided that includes means, such as an electrical energy store, such as a capacitor, for receiving an input based on a measured parameter during a measurement phase of a series of measurement and transmission phases. The apparatus also includes means, such as comparison circuitry, for comparing a voltage that is based on the input that is received over time to a threshold. The apparatus further includes means, such as control signal generation circuitry, for providing a control signal at least partially in response to satisfaction of the threshold to trigger a transmission phase in which the voltage is discharged. An estimate of the input that is based on the measured parameter is defined by the transmission phases.

The apparatus of an example embodiment also include means, such as a resonant circuit, for being inductively coupled to a primary circuit and for receiving energy from the inductively coupled primary circuit during the measurement phase. The resonant circuit includes an inductor configured to be inductively coupled to the primary circuit and a first capacitor disposed in parallel with the inductor. The apparatus of this example embodiment may also include first and second switches associated with the first capacitor and the electrical energy store, respectively. The first and second switches are responsive to the control signal so as to switchably replace the first capacitor with the electrical energy store during the transmission phase such that the electrical energy store is disposed in parallel with the inductor during the transmission phase. In an example embodiment, the respective capacitance of the first capacitor and the electrical energy store are equal. The resonant circuit of an example embodiment is configured to receive energy from the inductively coupled primary circuit in accordance with a resonant frequency. In this example embodiment, the control signal is provided for a single period as defined by the resonant frequency prior to returning to the measurement phase. The estimate of the input that is based on the measured parameter may also be based upon the threshold and the capacitance of the electrical energy store.

The apparatus of an example embodiment also includes means, such as a sensor, for measuring the parameter and providing the input that is based on the measured parameter. The apparatus of this example embodiment may also include means, such as a switch, responsive to the control signal, for switchably disconnecting the means, such as the sensor, for measuring the parameter from the means, such as the electrical energy store, for receiving the input during the transmission phase. The apparatus of an example embodiment also includes means, such as a switch, responsive to the control signal, for switchably disconnecting the means, such as the comparison circuitry, for comparing from the means, such as the electrical energy store, for determining the estimate of the input based upon a time between the transmission phases.

In a further example embodiment, an apparatus is provided that includes a primary circuit and a secondary circuit inductively coupled to the primary circuit in order to receive energy from the primary circuit. The secondary circuit includes means, such as a resonant circuit, for receiving energy from the primary circuit during a series of measurement and transmission phases. The apparatus also includes means, such as a sensor, for providing an input based on a measured parameter during a measurement phase and means, such as an electrical energy store, for receiving the input during the measurement phase. The apparatus further includes means, such as comparison circuitry, for comparing a voltage that is based on the input that is received over time to a threshold and means, such as control signal generation circuitry, for providing a control signal at least partially in response to satisfaction of the threshold to trigger a transmission phase in which the voltage is discharged and a voltage of a primary circuit is correspondingly increased.

The resonant circuit of an example embodiment includes an inductor configured to be inductively coupled to the primary circuit and a first capacitor disposed in parallel with the inductor. In this example embodiment, the apparatus may also include first and second switches associated with the first capacitor and the electrical energy store, respectively. The first and second switches are responsive to the control signal so as to switchably replace the first capacitor with the electrical energy store during the transmission phase such that the electrical energy store is disposed in parallel with the inductor during the transmission phase. In this example embodiment, the respective capacitances of the first capacitor and the electrical energy store may be equal. The apparatus of an example embodiment also includes means, such as processing circuitry, for determining an estimate of the input based upon a time between the transmission phases and, one embodiment, also based upon the threshold and a capacitance of the electrical energy store.

BRIEF DESCRIPTION OF THE DRAWINGS

Figure 1:
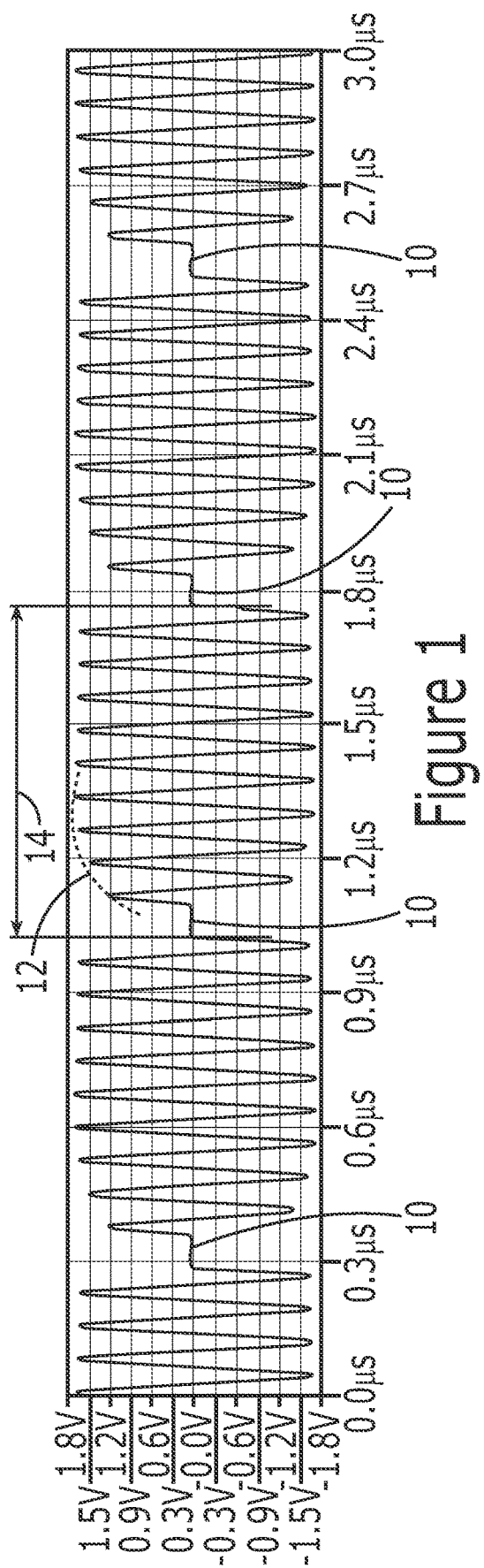
Figure 2:
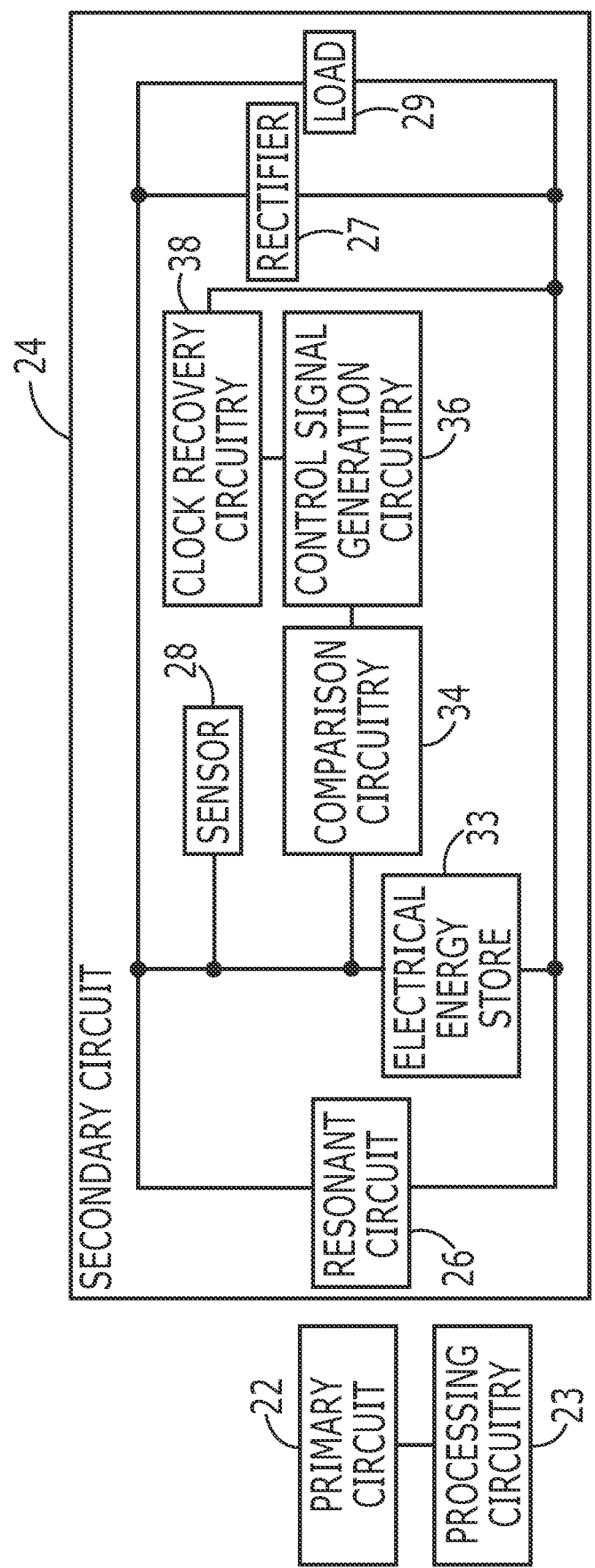
Figure 3:
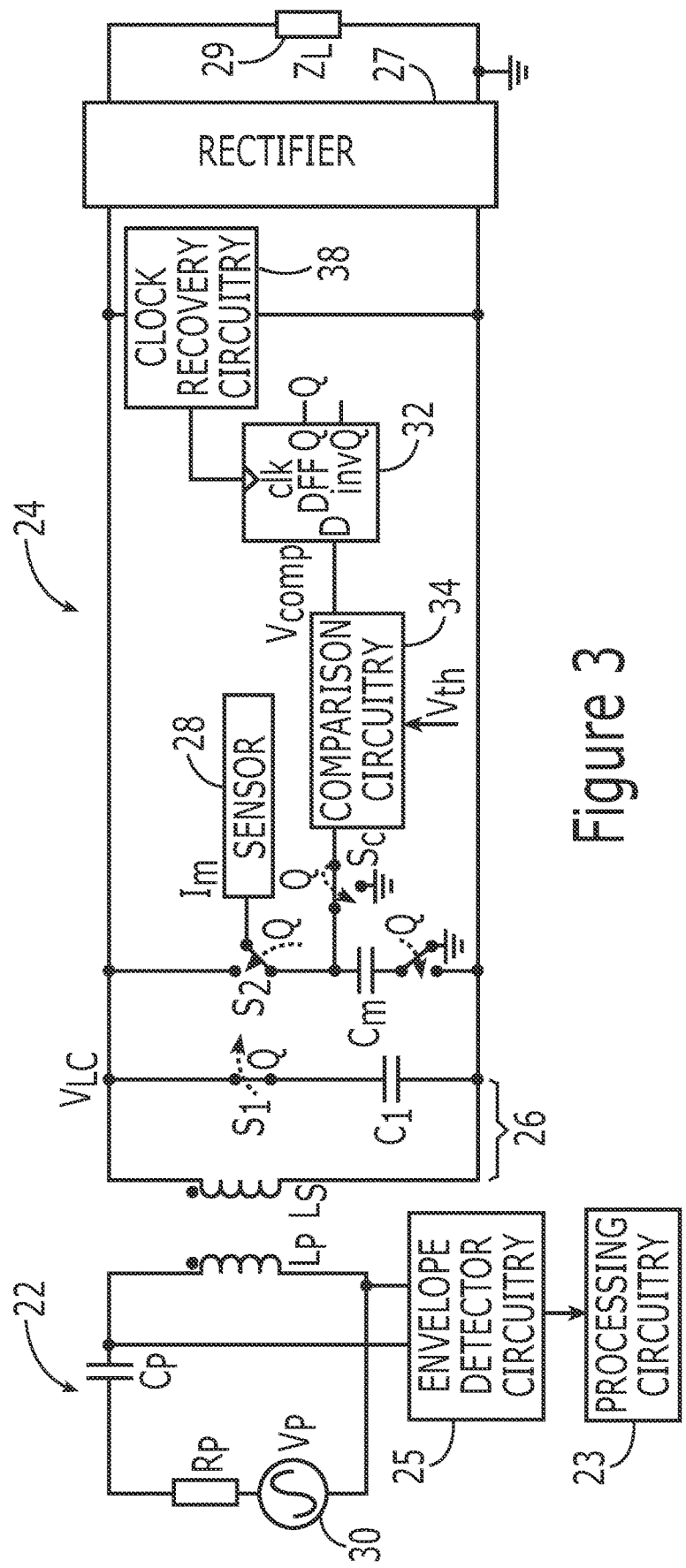
Figure 4:
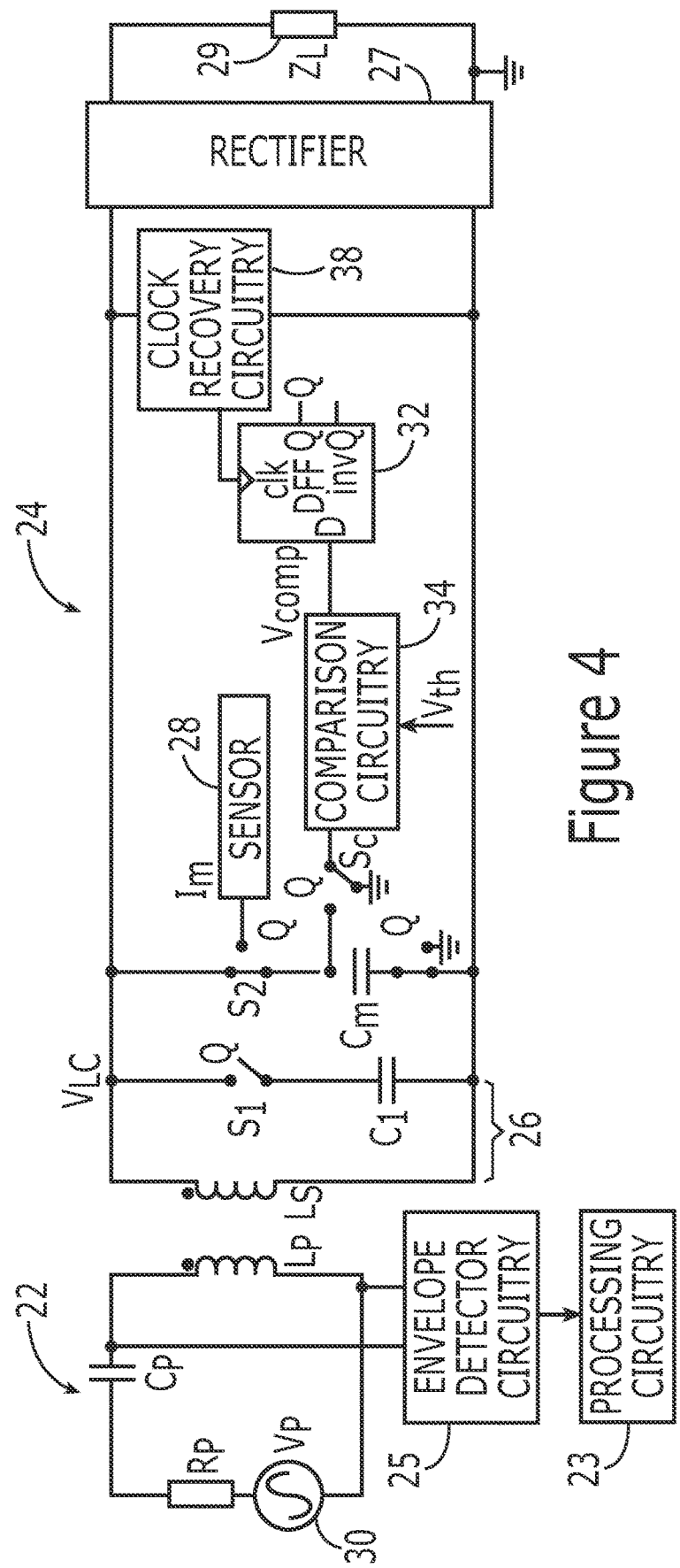
Figure 5:
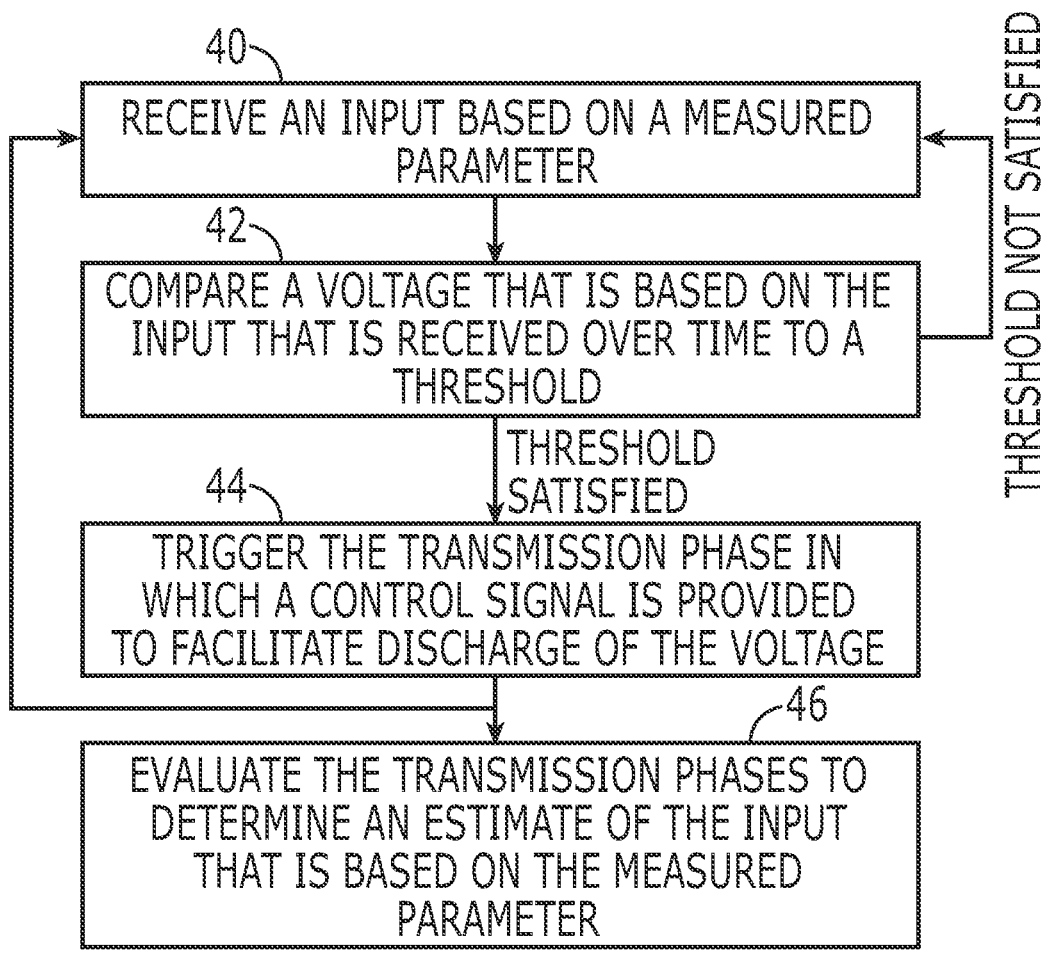
Figure 6:
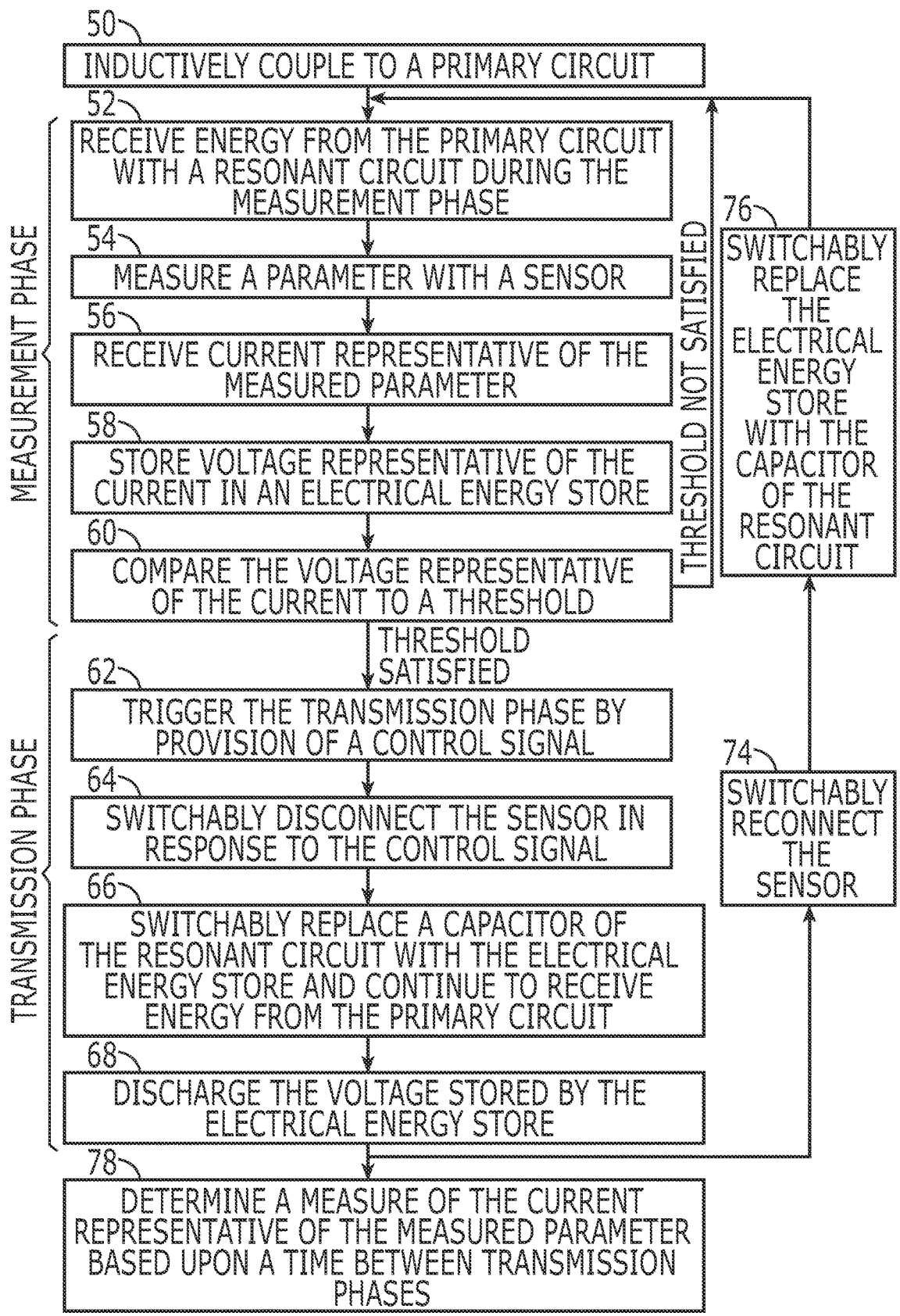
Figure 7:
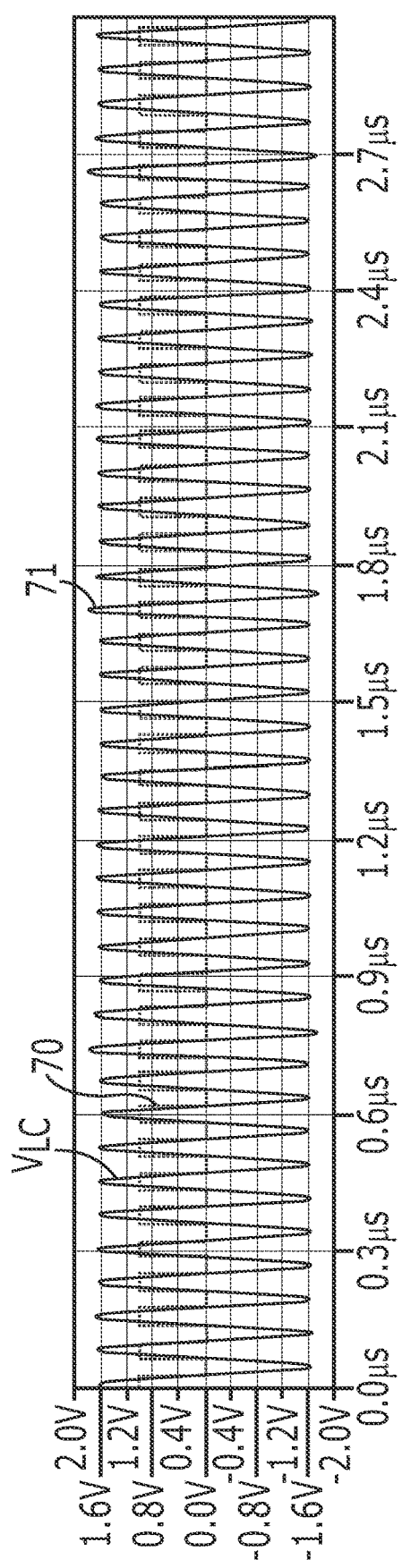
Figure 8:
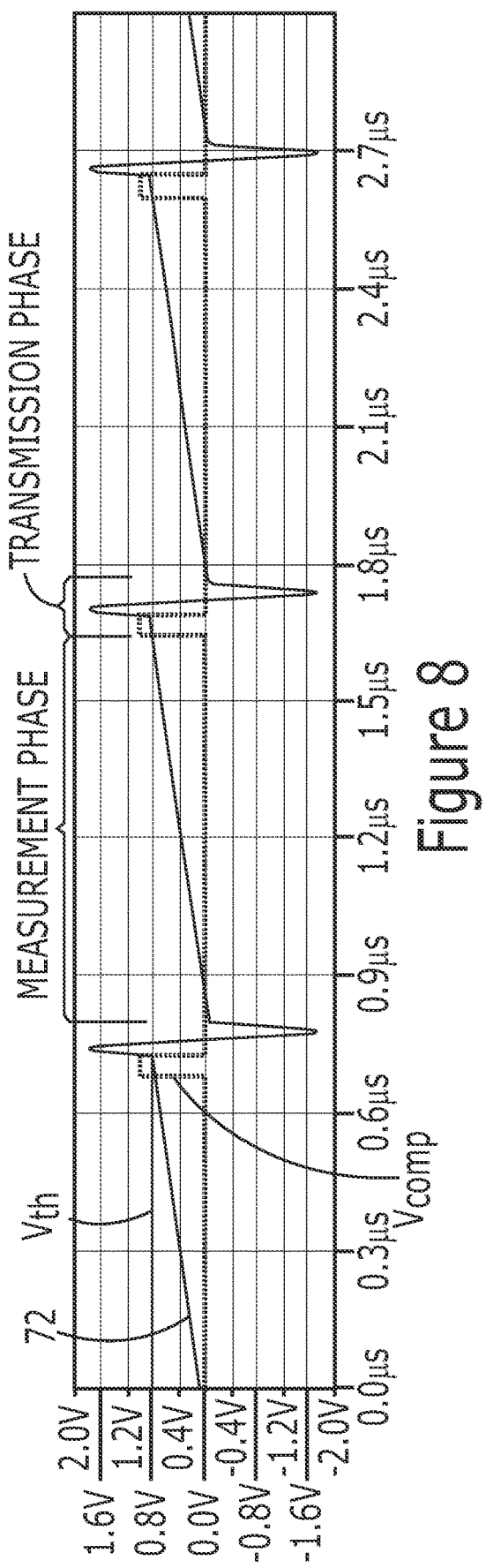
Figure 9:
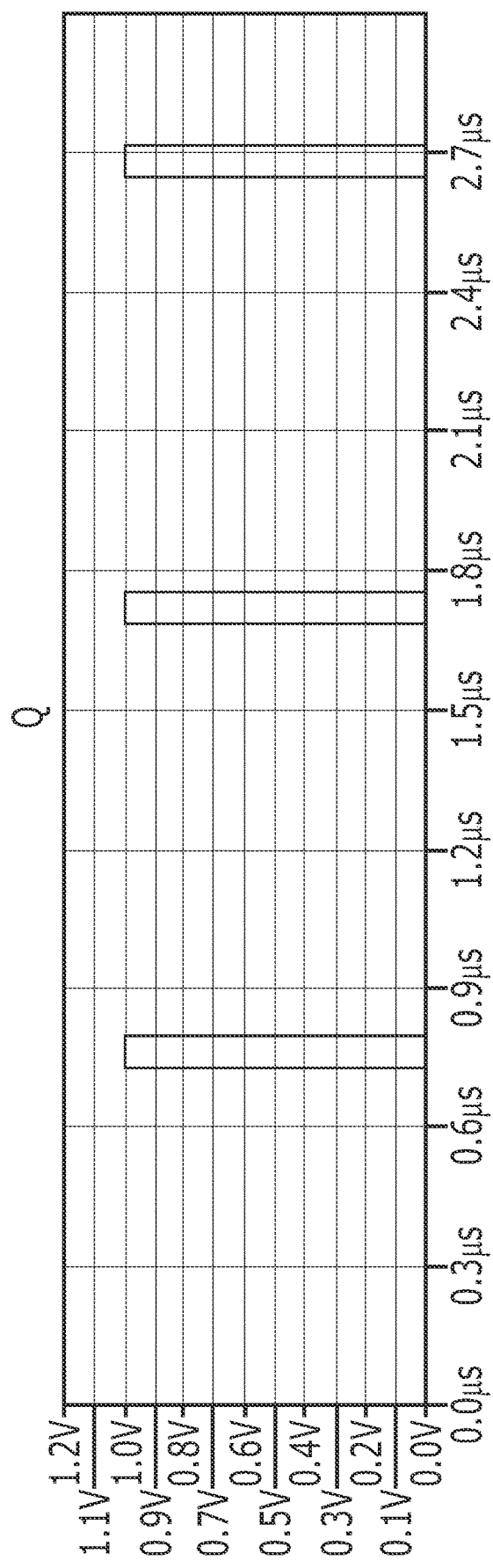
Figure 10:
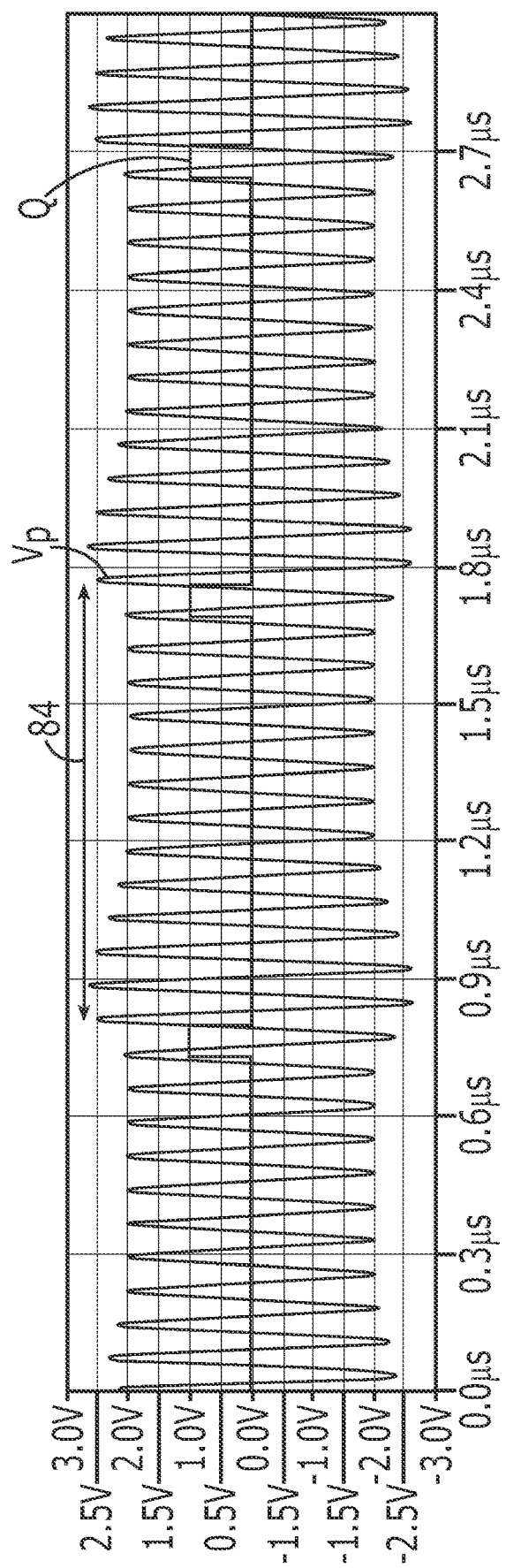
Figure 11:
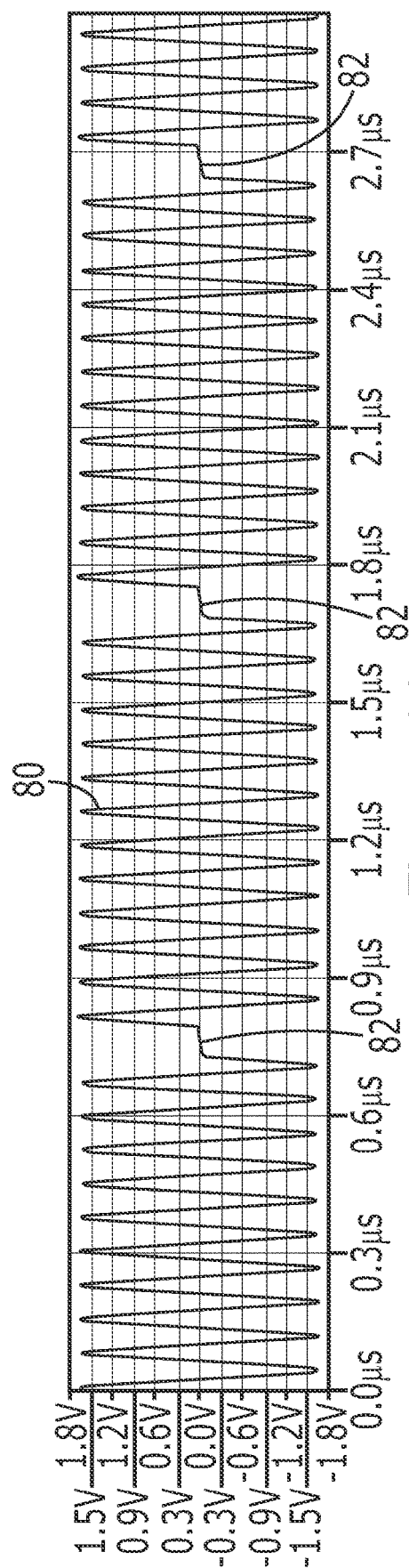
Figure 12:
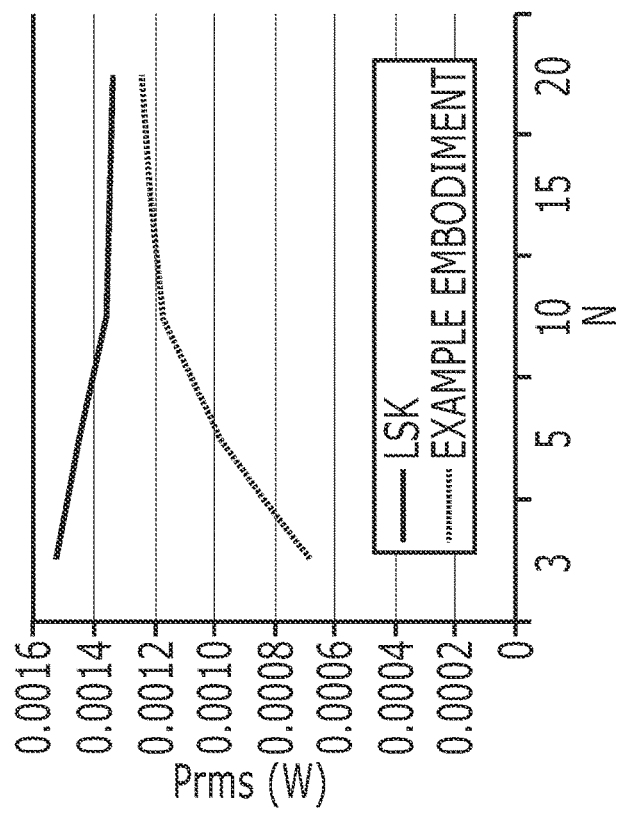
Figure 13:
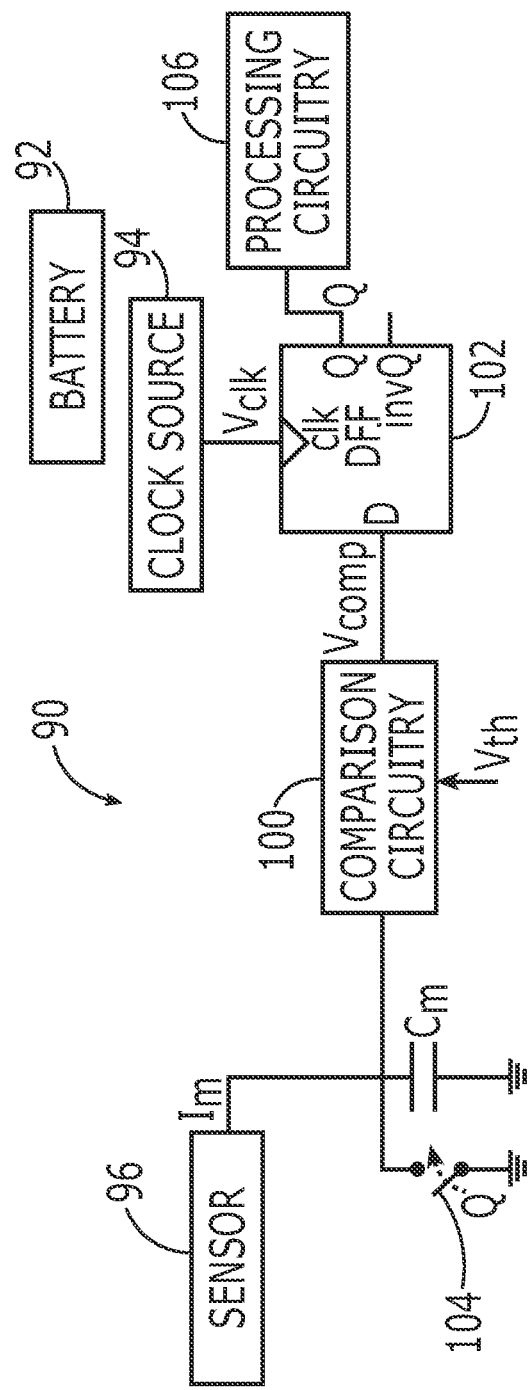

Having thus described certain embodiments of the invention in general terms, reference will now be made to the accompanying drawings, which are not necessarily drawn to scale, and wherein:

FIG. 1 depicts a waveform of the voltage across a resonant circuit of the secondary circuit which illustrates short circuiting of the resonant circuit during the transmission phase;

FIG. 2 is a block diagram of an apparatus in accordance with an example embodiment;

FIG. 3 is a circuit diagram of an apparatus in accordance with an example embodiment during a measurement phase;

FIG. 4 is a circuit diagram of an apparatus in accordance with an example embodiment during a transmission phase;

FIG. 5 is a flowchart illustrating the operations performed, such as by the apparatus of FIG. 2, in accordance with an example embodiment FIG. 6 is a more detailed flowchart illustrating the operations performed, such as by the apparatus of FIG. 2, in accordance with an example embodiment;

FIG. 7 illustrates a waveform of the voltage across the primary circuit which depicts a voltage rise during the transmission phase as well as a waveform generated by clock recovery circuitry in accordance with an example embodiment;

FIG. 8 illustrates the voltage stored by the electrical energy store over time relative to a threshold and an output of the comparison circuitry that is triggered once the voltage stored by the electrical energy store satisfies the threshold in accordance with an example embodiment;

FIG. 9 illustrates a waveform representative of a control signal generated based at least in part in response to satisfaction of the threshold by the voltage stored by the electrical energy store in accordance with an example embodiment;

FIG. 10 illustrates a waveform of the voltage across the primary circuit illustrating the rise in voltage following the transmission phase, the timing of which is represented for purposes of reference by the waveform of the control signal in accordance with an example embodiment;

FIG. 11 illustrates a waveform of the voltage across the first capacitor of the secondary circuit which illustrates the disconnection of the first capacitor from the resonant circuit during the transmission phase in accordance with an example embodiment;

FIG. 12 is a graphical representation of the efficiency with which an apparatus in accordance with an example embodiment operates relative to a conventional wireless device that relies upon LSK; and FIG. 13 is a circuit diagram of an apparatus in accordance with another example embodiment, such as may be embodied by a smart device or a medical device that includes a battery and an internal clock.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information," and similar terms may be used interchangeably to refer to data capable of being transmitted, received and/or stored in accordance with embodiments of the present invention. Thus, use of any such terms should not be taken to limit the spirit and scope of embodiments of the present invention.

Additionally, as used herein, the term 'circuitry' refers to (a) hardware-only circuit implementations (e.g., implementations in analog circuitry and/or digital circuitry); (b) combinations of circuits and computer program product(s) comprising software and/or firmware instructions stored on one or more computer readable memories that work together to cause an apparatus to perform one or more functions described herein; and (c) circuits, such as, for example, a microprocessor(s) or a portion of a microprocessor(s), that require software or firmware for operation even if the software or firmware is not physically present. This definition of 'circuitry' applies to all uses of this term herein, including in any claims. As a further example, as used herein, the term 'circuitry' also includes an implementation comprising one or more processors and/or portion(s) thereof and accompanying software and/or firmware. As another example, the term 'circuitry' as used herein also includes, for example, a baseband integrated circuit or applications processor integrated circuit for a mobile phone or a similar integrated circuit in a server, a cellular network device, other network device (such as a core network apparatus), field programmable gate array, and/or other computing device.

A method and apparatus are provided in accordance with an example embodiment in order to estimate a measured parameter. Although the method and apparatus may be employed in conjunction with a variety of applications, a method and apparatus of an example embodiment may be utilized in conjunction with the measurement of one or more parameters of a subject, such as a person, an animal or the like. The parameters of this example embodiment may be biological parameters indicative of the health or physical condition of the subject and may include, but are not limited to, glucose levels, lactase levels, oxygen levels, PH levels or the like.

As described below, the apparatus of an example embodiment may be embodied by a wirelessly powered device that is worn by or implanted in the subject. By being wirelessly powered, the device may, but need not, include a battery and, instead, the energy necessary for the operation of the device including measurement of the parameter and the provision of signals indicative of the measured parameter may be provided by another device, such as may be indicatively coupled to the wirelessly powered device worn by or implanted in the subject. Alternatively, the apparatus may be embodied by a device that is not wirelessly powered but that may, instead, include another source of energy, such as an internal battery. This type of device may also be worn by the subject so as to measure the parameter and to provide signals indicative of the measured parameters.

In an example embodiment depicted in FIG. 2, an apparatus 20 that is wirelessly powered and that may, but need not include a battery or other source of power is depicted. In order to provide for the wireless provision of power, the apparatus includes primary and secondary circuits 22, 24 that are inductively coupled such that the primary circuit provides energy to a resonant circuit 26 of the secondary circuit to enable operation of the secondary circuit. As shown in FIG. 2, the secondary circuit includes a rectifier 27 for converting the AC voltage provided by the inductively coupled primary circuit to DC voltage which, in turn, is provided to the load 29 of the secondary circuit. The load represents the overall impedance of all circuitry that uses DC power. In this example embodiment, the load includes the sensor 28, the comparison circuitry 34, the control signal generation circuitry 36 and the clock recovery circuitry 38 as described below, but the load may include any other circuits which perform different functions and use DC power.

The secondary circuit 24 may be embodied by a device that may be worn by a subject in order to measure a desired parameter. Since the secondary circuit of this example embodiment is wirelessly powered and may correspondingly transmit data representative of the measured parameter in a wireless manner, the secondary circuit may also be embodied by a device that may be inserted or implanted in the subject so as to measure the desired parameter. Although the primary circuit may also be embodied by a device that is worn by the subject, the primary circuit may, instead, be embodied by a device that is neither worn by nor implanted in the subject, but that is, instead, positioned proximate the device that embodies the secondary circuit so as to provide for inductive coupling therebetween. For example, the primary circuit may be provided by a smart phone or other smart device or any other device configured to provide power inductively to the secondary circuit and that is carried by and/or attached to the clothing of a user in the vicinity of the secondary circuit.

As shown in more detail in FIG. 3, the primary circuit 22 of an example embodiment includes a power supply 30, such as a voltage source, which provides, for example, an input AC voltage having a magnitude $V_p$. The power supply may have an internal impedance as represented by resistance $R_p$ in FIG. 3. The primary circuit of this example embodiment also include a capacitor $C_p$ and an inductor $L_p$ that are connected in series with the power supply. As shown in FIG. 2 and, more detail, in FIG. 3, the secondary circuit 24 includes a resonant circuit 26 that is inductively coupled to the primary circuit. The resonant circuit of this example embodiment includes an inductor $L_s$ and a first capacitor $C_1$ in parallel with the inductor $L_s$ to form an LC tank circuit. The inductors of the primary circuit and the resonant circuit of the secondary circuit are inductively coupled such that power is wirelessly transferred from the primary circuit to the secondary circuit for storage, at least temporarily, by the first capacitor $C_1$.

The primary circuit 22 has a resonant frequency as defined by the capacitor $C_p$ and the inductor $L_p$. For example, the resonant frequency f may be defined as $f=(1/(2\pi(L_1C_1)^{1/2})$. Likewise, the resonant circuit 26 of the secondary circuit 24 has a resonant frequency as defined by the inductor $L_s$ and the first capacitor $C_1$. In an example embodiment, the resonant frequency of the primary circuit equals the resonant frequency of the secondary circuit.

The secondary circuit 24 operates alternately in a measurement phase and a transmission phase. In the measurement phase, the parameter of interest is measured, such as by a sensor 28. In the transmission phase, data representative of the measured parameter is transmitted, such as from the secondary circuit 24 to the primary circuit 22, to facilitate subsequent estimation of the measure parameter, such as by processing circuitry 23 as shown in FIG. 2. By way of illustration, FIG. 3 depicts the secondary circuit during the measurement phase and FIG. 4 depicts the same secondary circuit during the transmission phase. In order to measure the parameter, the secondary circuit includes or is in communication with the sensor, such as a biosensor, configured to measure the parameter of interest and to provide a signal, such as current, having a value that is based upon, such as by being representative of, e.g., proportional to, the measured parameter. Although the secondary circuit may include a variety of different types of sensors depending upon the parameter to be measured, the sensor of one example embodiment is amperometric electrochemical biosensor.

The secondary circuit 24 of an example embodiment will be described in more detail in conjunction with the operation of the secondary circuit. In this regard, FIG. 5 depicts the operations performed by an apparatus 20 that includes the secondary circuit in conjunction with the provision of a series of measurement and transmission in accordance with an example embodiment. As shown in block 40, during a measurement phase, the apparatus 20 includes means, such as an electrical energy store 33, such as a measurement capacitor $C_m$, for receiving an input based on a measured parameter, such as input provided by the sensor 28. The apparatus of this example embodiment also includes means, such as the comparison circuitry 34, for comparing a voltage that is based on the input that is received over time, such as a voltage maintained by the electrical energy store, such as the measurement capacitor $C_m$, to a threshold. See block 42. In an instance in which the threshold is not satisfied, the measurement phase continues with input continuing to be received which, in turn, adds to the voltage that is maintained, such as by the electrical energy store.

In an instance in which the threshold is satisfied, however, the apparatus 20 includes means, such as the control signal generation circuitry 36 as shown in FIG. 2 which may be embodied by a type of gated latch, such as a flip-flop, e.g., a D flip-flop 32 as shown in FIGS. 3 and 4, for triggering the transmission phase in which a control signal is provided to facilitate discharge of the voltage stored by the electrical energy store 33 such as the measurement capacitor $C_m$. See block 44 of FIG. 5. Upon completion of the transmission phase, the measurement phase recommences with the receipt of the input based on the measured parameter as shown in block 40. Additionally, the apparatus of this example embodiment includes means, such the processing circuitry 23 or the like, for evaluating the transmission phases to determine an estimate of the input that is based on the measured parameter, as shown in block 46 of FIG. 5 and described in more detail below.

In this regard, FIG. 6 also depicts the operations performed by an apparatus 20 that includes the secondary circuit 24 in accordance with an example embodiment, albeit in more detail than in FIG. 5. As shown in block 50, the apparatus includes means for inductively coupling the primary circuit 22 and the secondary circuit, such as by the inductive coupling of the inductor $L_p$ of the primary circuit and the inductor $L_s$ of the resonant circuit 26 of the secondary circuit. During the measurement phase, the secondary circuit also includes means, such as the resonant circuit, for receiving energy from the primary circuit that is inductively coupled thereto. See block 52. In the illustrated embodiment, the energy that is received by the resonant circuit may be stored, at least temporarily, by a first capacitor $C_1$ of the resonant circuit.

As shown in block 54, the apparatus 20 includes means, such as the sensor 28, for measuring a parameter and providing a signal representative of the measured parameter, such as by being proportional to the measured parameter. The secondary circuit 24 also includes means for receiving an input based on the measured parameter during the measurement phase. See block 56. In this regard, the input may be the signal provided by the sensor and representative of the measured parameter. For example the signal may be a current having a value that is representative of, e.g., proportional to, the measured parameter. The means for receiving the input may be embodied by an electrical energy store 33, such as a measurement capacitor $C_m$. In this example embodiment, the secondary circuit also includes means for storing a voltage that is based on the input, such as the current, that is received over time. See block 58. For example, the means for storing the voltage representative of the input may also be embodied by the electrical energy store, such as a measurement capacitor $C_m$. In this example embodiment in which the input provided by the sensor is a current having a value that is based on, such as being representative of, e.g., proportional to, the measured parameter, the electrical energy store, such as the measurement capacitor $C_m$, may be configured to receive the current and to store voltage representative of the current and, in turn, the measured parameter.

The apparatus 20, such as the secondary circuit 24, of this example embodiment also includes means for comparing the voltage that is based on the input that is received over time to a threshold $V_{th}$, such as a predefined voltage. See block 60. In an example embodiment, the means for comparing the voltage to a threshold may be embodied by comparison circuitry 34 as shown in FIGS. 2-4, such as a comparator, configured to compare the voltage of the electrical energy store 33 representative of the current that has been received over time and, in turn, representative of the measured current to a voltage threshold $V_{th}$. In an instance in which the threshold does not satisfy the threshold, such as in an instance in which the voltage of the electrical energy store is less than the threshold, the measurement phase continues with the sensor 28 continuing to measure the parameter and to provide current representative of, e.g., proportional to, the measured parameter and the electrical energy store continuing to store a voltage that increases over time as additional current is received until such time that the voltage stored by the electrical energy store satisfies the threshold, such as by equaling or exceeding the threshold.

In an instance in which the threshold is satisfied, such as in an instance in which the voltage stored by the electrical energy store 33 equals or exceeds the voltage threshold, the apparatus 20, such as the secondary circuit 24, switches from the measurement phase to the transmission phase in which data representative of the measured parameter is provided to the primary circuit 22 and, in turn, to the processing circuitry 23 for evaluation. As shown in block 62 of FIG. 6, the apparatus, such as the secondary circuit, includes means, such as control signal generation circuitry 36 as shown in FIG. 2, for triggering the transmission phase in which a control signal is provided to facilitate discharge of the voltage stored by the electrical energy store in response to satisfaction of the threshold. Although the control signal generation circuitry may be configured in various manners, the secondary circuit depicted in FIGS. 3 and 4 includes a type of gated latch, such as a flip-flop, e.g., a D flip-flop 32, responsive to the comparison circuitry 34 and configured to generate the control signal in an instance in which the comparison circuitry indicates that the threshold is satisfied.

In the illustrated embodiment, the control signal generation circuitry 36 is clocked, such as by clock signal provided by a clock recovery circuitry 38 of FIGS. 2-4. The clock recovery circuitry may be provided by any circuit configured to provide a clock signal, such as a clock signal synchronized with another, e.g., sinusoidal, signal. For example, the clock recovery circuitry may be embodied by a zero crossing detector circuit. Although the clock recovery circuitry may provide various types of clock signals, the clock recovery circuitry of an example embodiment is responsive to the voltage $V_{LC}$ across the resonant circuit 26. As shown in FIG. 7, the voltage $V_{LC}$ across the resonant circuit is an alternating signal, such as a sinusoidal signal. Responsive to the voltage $V_{LC}$ across the resonant circuit, the clock recovery circuitry produces a clock signal in the form of a rectangular wave 70 having the same frequency as the alternating voltage across the resonant circuit. In the example embodiment, the clock recovery circuitry generates a rectangular wave having a 50% duty cycle, a maximum amplitude that is positive, but less than the maximum amplitude of the alternating voltage $V_{LC}$ across the resonant circuit and a minimum amplitude of 0. For example, the maximum amplitude of the rectangular wave may be based on, such as by being no more than, the DC power supply voltage level and, in some embodiments, may be 1 V, 3V, 5 V, etc.

In the example embodiment depicted in FIGS. 3 and 4, the flip flop 32 is configured to generate a control signal that coincides with the first rising edge of the clock signal provided by the clock recovery circuitry 38 following receipt of a signal from the comparison circuitry 34 indicating that the voltage stored by the electrical energy store 33 satisfies the voltage threshold $V_{th}$. With reference to FIG. 8 by way of example, the voltage 72 stored by the electrical energy store is shown to increase over time as additional current is provided by the sensor 28 representative of the measured parameter, such as by being proportional to the measured parameter. Once the voltage that is stored by the electrical energy store satisfies the threshold, such as by equaling or exceeding the threshold, the comparison circuitry provides an output $V_{comp}$ as shown in FIG. 8 indicating that the threshold has been satisfied. Once the comparison circuitry has provided the signal indicating satisfaction to the threshold, the control signal generation circuitry is configured to provide a control signal Q that commences concurrent with the rising edge of the next clock pulse provided by the clock recovery circuitry. In this regard, FIG. 9 illustrates the control signal Q that is provided by the clock signal generation circuitry.

Upon generation of the control signal Q, the secondary circuit 24 is reconfigured during the transmission phase. In this regard and in response to the control signal, the secondary circuit includes means, such as a sensor switch $S_s$, for switchably disconnecting the means, such as the sensor 28, for measuring the parameter from the means, such as the electrical energy store 33, for receiving the input during the transmission phase. See block 64 of FIG. 6. In this regard and in response to the control signal, the sensor switch $S_s$ of the secondary circuit of the embodiment of FIGS. 3 and 4 is in a closed position during the measurement phase in which the control signal is not provided so as to connect the sensor to the electrical energy store. In response to the control signal, however, the sensor switch $S_s$ transitions to an open position which disconnects the sensor from the electrical energy store such that input is not provided by the sensor to the electrical energy store during the transmission phase.

The secondary circuit 24 also includes means, such as a comparator switch $S_c$, for switchably disconnecting the means, such as the comparison circuitry 34, for comparing from the means, such as the electrical energy store 33, for receiving the input during the transmission phase. In this regard, the comparator switch $S_c$ of the secondary circuit is in a closed position during the measurement phase in which a control signal is not provided so as to connect the comparison circuitry to the electrical energy store. In response to the control signal, however, the comparator switch $S_c$ transitions to a different position in which the comparison circuitry is disconnected from the electrical energy store and is, instead, connected to ground during the transmission phase.

As is also shown in FIGS. 3 and 4, the secondary circuit 24 of an example embodiment further includes first and second switches $S_1$, $S_2$ associated with, such as by being serially connected to, e.g., in line with, the first capacitor $C_1$ of the resonant circuit 26 and the electrical energy store 33, respectively. The secondary circuit of this example embodiment includes means, such as first and second switches that are also responsive to the control signal, for switchably replacing the first capacitor with the electrical energy store during the transmission phase such that the electrical energy store is disposed in parallel with the inductor $L_s$ of the resonant circuit during the transmission phase. See block 66. In this regard, during the measurement phase in which a controls signal is not provided, the first switch $S_1$ has a first position, e.g., a closed position, that connects the first capacitor $C_1$ in parallel with the inductor $L_s$ of the resonant circuit and the second switch $S_2$ has a first position that connects with electrical energy store to ground. In response to the control signal, however, the first and second switches are transitioned to the respective second positions with the second position of the first switch $S_1$ being an open position such that first capacitor $C_1$ is no longer electrically connected in parallel with the inductor $L_s$ of the resonant circuit. Conversely, the second position of the second switch $S_2$ does place the electrical energy store in parallel with the inductor $L_s$ during the transmission phase such that the electrical energy store replaces the first capacitor $C_1$ in the resonant circuit during the transmission phase.

During the transmission phase, the resonant circuit 26 is not short circuited. Instead, the resonant circuit is reconfigured so as to be formed by the inductor $L_s$ and the electrical energy store 33, which are connected in parallel. As such, energy can continue to be transferred inductively from the primary circuit 22 to the secondary circuit 24 not only during the measurement phase, but also during the transmission phase, thereby increasing the efficiency with which energy is transferred to the secondary circuit and increasing the consistency with which energy is provided to the load. In order to ensure that the resonant circuit of the secondary circuit has the same resonant frequency during the measurement phase and in the transmission phase and remains the same as the resonant frequency of the primary circuit when the electrical energy store replaces the first capacitor $C_1$ in the resonant circuity, the capacitance of the electrical energy store of an example embodiment equals the capacitance of the first capacitor $C_1$ of the resonant circuit.

As a result of the switchable connection of the electrical energy store 33 in parallel with the inductor $L_s$, the secondary circuit 24 includes means, such as the electrical energy store, the first and second switches $S_1$, $S_2$ and/o the inductor $L_s$, for discharging the voltage stored by the electrical energy store in response to the input representative of the measured parameter, such as provided by the sensor 28, such that the voltage $V_{LC}$ across the resonant circuit 26 of the secondary circuit 24 is temporarily increased and correspondingly, the voltage across the inductor $L_p$ of the primary circuit 22 is increased as a result of the inductive coupling of the primary and secondary circuits. See block 68. In this regard, FIG. 10 depicts the control signal Q which defines the transmission phase as well as the voltage $V_p$ that appears across the inductor $L_p$ of the primary circuit 22. As shown, the voltage $V_p$ across the inductor of the primary circuit increases temporarily immediately following and in response to the transmission phase prior to decaying to the level defined by the power supply 30 once the voltage stored by the electrical energy store has been discharged. Similarly, FIG. 7 depicts the temporary voltage rise 71 across the resonant circuit 26 of the secondary circuit 24 during the transmission phase.

In an example embodiment, the control signal generation circuitry 36 is configured to provide the control signal for only a single period as defined by the resonant frequency. In this regard, the repositioning of the comparator switch $S_c$ associated with the comparison circuitry 34 during the transmission phase to be switchably connected to ground as opposed to the electrical energy store 33 causes the output $V_{comp}$ of the comparator circuitry to change states since the voltage threshold $V_{th}$ is no longer satisfied. Thus, upon the next rising edge of the clock signal provided by the clock recovery circuitry 38, the control signal generation circuitry no longer provides the control signal. The secondary circuit 24 of an example embodiment therefore includes means, such as the control signal generation circuitry, the sensor switch $S_s$ or the like, for switchably reconnecting the sensor to the electrical energy store, such as by returning the sensor switch to the closed position in an instance in which the control signal Q is no longer provided. See block 74 of FIG. 6. In addition, the secondary circuit of this example embodiment may include means for switchably replacing the electrical energy store with the first capacitor C1 of the resonant circuit 26 in response to the control signal no longer being provided. See block 76. In this regard, the means for switchably replacing the electrical energy store with the first capacitor C1 may include the first and second switches $S_1$, $S_2$ that are returned to their respective first positions such that the first capacitor $C_1$ is connected in parallel with the inductor $L_s$ of the resonant circuit 26 and the electrical energy store is connected to ground. In response to the control signal no longer being provided, the comparator switch $S_c$ is also configured to return to the closed position so as to connect the comparison circuitry to the electrical energy store. As such, the secondary circuit 24 returns to the measurement phase and the voltage stored by the electrical energy store again increases from zero as shown in FIG. 8, as a result to the discharge of the voltage during the transmission phase, until the voltage satisfies the threshold $V_{th}$ and the transmission phase is again triggered. Thus, the secondary circuit alternates between the measurement and transmission phases in order to repeatedly provide the primary circuit with data representative of the measured parameter.

By way of example of the switchable connection and disconnection of the first capacitor $C_1$ in parallel with the inductor $L_s$ of the resonant circuit 26, FIG. 11 depicts the voltage $V_{LC}$ across the first capacitor and, in turn, across the resonant circuit. During the measurement phase, an alternating voltage waveform 80 appears across the first capacitor as a result of the inductive coupling of the resonant circuit with the primary circuit 22 that provides a corresponding alternating voltage waveform. During the transmission phase, however, no voltage appears across the first capacitor as a result of the switchable disconnection of the first capacitor from the inductor $L_s$ as designated 82 in FIG. 11.

The apparatus 20 of an example embodiment also includes means, such as processing circuitry 23, a computer program product or the like, for determining an estimate of the input that is based on the measured parameter as defined by the transmission phases. See block 78 of FIG. 6. The processing circuitry of an example embodiment may include or otherwise be in communication with a memory device, such as via a bus, for passing information therebetween. The memory device may be non-transitory and may include, for example, one or more volatile and/or non-volatile memories. In other words, for example, the memory device may be an electronic storage device (for example, a computer readable storage medium) comprising gates configured to store data (for example, bits) that may be retrievable by a machine (for example, a computing device like the processor). The memory device may be configured to store information, data, content, applications, instructions, or the like for enabling the apparatus to carry out various functions in accordance with an example embodiment of the present invention. For example, the memory device could be configured to buffer input data for processing by the processor. Additionally or alternatively, the memory device could be configured to store instructions for execution by the processing circuitry.

The processing circuitry 23 may be embodied in a number of different ways. For example, the processing circuitry may be embodied as one or more of various hardware processing means such as a processor, a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processing circuitry may include one or more processing cores configured to perform independently. A multi-core processor may enable multiprocessing within a single physical package. Additionally or alternatively, the processing circuitry may include one or more processors configured in tandem via the bus to enable independent execution of instructions, pipelining and/or multithreading.

In an example embodiment, the processing circuitry 23 may be configured to execute instructions stored in the memory device or otherwise accessible to the processing circuitry. Alternatively or additionally, the processing circuitry may be configured to execute hard coded functionality. As such, whether configured by hardware or software methods, or by a combination thereof, the processing circuitry may represent an entity (for example, physically embodied in circuitry) capable of performing operations according to an embodiment of the present invention while configured accordingly. Thus, for example, when the processing circuitry is embodied as an ASIC, FPGA or the like, the processing circuitry may be specifically configured hardware for conducting the operations described herein. Alternatively, as another example, when the processing circuitry is embodied as an executor of software instructions, the instructions may specifically configure the processing circuitry to perform the algorithms and/or operations described herein when the instructions are executed. However, in some cases, the processing circuitry may be a processor of a specific device (for example, a computing device) configured to employ an embodiment of the present invention by further configuration of the processor by instructions for performing the algorithms and/or operations described herein. The processing circuitry may include, among other things, a clock, an arithmetic logic unit (ALU) and logic gates configured to support operation of the processing circuitry.

The estimate of the input, such as the current provided by the sensor 28 representative of the measured parameter, such as proportional to the measured parameter, is at least partly defined by the time between the transmission phases, such as the time between consecutive transmission phases. In an example embodiment, the time between the transmission phases is defined as the time that lapses between an increase in the voltage across the inductor $L_p$ of the primary circuit 22, such as in response to discharge of the electrical energy store 33, during a first transmission phase and the increase in the voltage across the inductor of the primary circuit, such as in response to discharge of the electrical energy store during the next, such as a second, transmission phase, as shown by the period 84 in FIG. 10. As shown in FIGS. 3 and 4, the primary circuit 22 may also include envelope detection circuitry 25 configured to detect the increase in the voltage across the inductor of the primary circuit. In this example embodiment, the processing circuit is responsive to the envelope detection circuitry for determining the time between the transmission phases. In an example embodiment, the estimate of the input, such as the current, is not only based upon the time $T_m$ between consecutive the transmission phases, but also on the threshold $V_{th}$ and the capacitance $C_m$ of the electrical energy store. In this regard, the processing circuitry of an example embodiment may be configured to estimate the current $I_m$ provided by the sensor that is representative of, e.g., proportional to, the measured parameter as follows:

$$I_m = V_{th} * Cm/Tm$$

The method and apparatus 20 of this example embodiment therefore facilitate the estimation of a measured parameter, such as any of various biological parameters of a subject that may be measured by a sensor 28. In this embodiment that includes both a primary circuit 22 and a secondary circuit 24 that are inductively coupled, the method and apparatus provide for data transfer, such a data representative of the measured parameter, without short circuiting the resonant circuit 26 of the secondary circuit. Thus, energy may continue to be provided by the primary circuit to the secondary circuit and, in turn, to a rectifier 27 of the secondary circuit not only during the measurement phase in which the parameter is being measured, but also during the transmission phase in which data is transferred from the secondary circuit to the primary circuit. Thus, the secondary circuit receives more consistent power and, as the result, operates more efficiently in terms of power transfer and utilization due to a shorter resonance recovery time interval relative to the use of LSK, while also providing for reliable data transfer and the accurate estimation of the measured parameter.

In this regard, FIG. 12 depicts the root mean square power (Prms) delivered to the load 29 by an apparatus 20 of an example embodiment relative to an apparatus operating in accordance with LSK. As such, the apparatus of an example embodiment delivers more power to the load than an apparatus operating in accordance with LSK, thereby evidencing the increased efficiency with respect to the delivery of power to the load. While the apparatus of an example embodiment is more efficient than an apparatus operating in accordance with LSK for a measurement phase having any number N of clock cycles, instances in which the data transfer occurs more frequently, such as every three clock cycles or five clock cycles, exhibit even greater relative efficiencies as a result of the more frequent transition period that may be overcome with an apparatus operating in accordance with LSK.

Although an example of the apparatus 20 has been described above in conjunction with FIGS. 2-4, the apparatus may be differently embodied while still providing an estimate of a measured parameter in accordance with the present disclosure. For example, the embodiment of the apparatus described heretofore includes primary and secondary circuits 22, 24 that are inductively coupled such that the secondary circuit need not include a battery or an internal clock. Instead, the energy associated with operation of the secondary circuit is provided by the inductive coupling to the primary circuit and the clock signal of the secondary circuit is derived from the alternating waveform inductively coupled from the primary circuit to the secondary circuit. In other embodiments, however, the apparatus may be embodied by a device that includes a battery and an internal clock. By way example, FIG. 13 depicts an apparatus 90 according to another example that includes a battery 92 and a clock source 94, such as an internal clock source. Although the device that embodies the apparatus of FIG. 13 may be any of a variety of devices, the device of one embodiment is a smart device, such as a smart phone, a fitness tracker or a variety of other personal medical devices.

In this example embodiment, the apparatus 90 includes a sensor 96 and, during the measurement phase, the sensor provides input, such as a current, to an electrical energy store, such as a measurement capacitor $C_m$, with the input, such as the current, being representative of a measured parameter, such as by being proportional to the measured parameter. The voltage stored by the electrical energy store is compared, such as by comparison circuitry 100, e.g., a comparator, to a threshold voltage $V_{th}$. In an instance in which the voltage stored by the electrical energy store satisfies the threshold, such as by equaling or exceeding the threshold, the comparison circuitry generates an output $V_{comp}$ and control signal generation circuitry, such as a type of gated latch, such as a flip-flop, e.g., a D flip-flop 102 in the illustrated embodiment, is responsive to the output of the comparison circuitry and generates the control signal concurrent with the rising edge of the first clock signal following the generation of the output $V_{comp}$ by the comparison circuit. In this example embodiment, the clock signal may be provided by the clock source 94.

In response to the control signal Q, the apparatus 90 of this example embodiment transitions to the transmission phase. In the transmission phase, a switch 104 is closed such that the sensor 96, the electrical energy store, such as a measurement capacitor $C_m$, and the comparison circuitry 100 are all connected to ground. As the input to the comparison circuitry is now connected to ground, the voltage threshold $V_{th}$ is no longer satisfied such that the comparison circuitry also no longer generates an output $V_{comp}$. Thus, concurrent with the rising edge of the next clock cycle, the control signal generation circuitry 102 no longer generates the control signal Q such that transmission phase ends and the measurement phase recommences with the opening of the switch.

As described above, the apparatus 90 of this example embodiment also alternates between the measurement and transmission phases. The apparatus of this example embodiment may also include or be associated with processing circuitry 106 that is configured to determine an estimate of the input provided by the sensor 96, such as a current provided by the sensor, that is based on, such as by being representative of, the measured parameter, e.g., proportional to the measured parameter. The processing circuitry is configured to determine the estimate based upon the transmission phases, such as the time that lapses between consecutive transmission phases. In this example embodiment, the processing circuitry is configured to determine the time between consecutive transmission phases based upon the time between consecutive control signals generated by the flip flop 102. As described above, the estimate of the input, such as the current, is not only based upon the time Tm between consecutive transmission phases (as defined in this example by the time between consecutive control signals generated by the control signal generation circuitry), but also on the threshold $V_{th}$ and the capacitance $C_m$ of the electrical energy store, such as a measurement capacitor $C_m$. In this regard, the processing circuitry of an example embodiment may again be configured to estimate the current provided by the sensor that is representative of, e.g., proportional to, the measured parameter as follows:

$$I_m = V_{th} * Cm/Tm$$

As described above, the processing circuitry 23, 106 is configured to determine a measure of the current representative of, such as proportional to, the measured parameter. In an example embodiment, the processing circuitry may be configured to operate based upon the execution of software including one or more computer program instructions. Alternatively, all or some of the functionality of the processing circuitry may be replaced by computer program instructions in other embodiments. In either instance, the computer program instructions may be stored by a memory device and executed by the processing circuitry or some other computing device. As will be appreciated, any such computer program instructions may be loaded onto a computer or other programmable apparatus (for example, hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the functions described above. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified above with respect to the processing circuitry.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Furthermore, in some embodiments, additional optional operations may be included. Modifications, additions, or amplifications to the operations above may be performed in any order and in any combination.

Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus comprising:
an electrical energy store configured to receive an input based on a measured parameter during a measurement phase of a series of measurement and transmission phases;
comparison circuitry configured to compare a voltage that is based on the input that is received over time to a threshold;
control circuit generation circuitry configured to provide a control signal at least partially in response to satisfaction of the threshold to trigger a transmission phase in which the voltage is discharged; and
a first switch associated with a first capacitor and a second switch associated with an electrical energy store, wherein the first switch and second switch are responsive to the control signal so as to switchably replace the first capacitor with the electrical energy store during the transmission phase,
wherein an estimate of the input that is based on the measured parameter is defined by the transmission phases.

2. An apparatus according to claim 1 further comprising a resonant circuit configured to be inductively coupled to a primary circuit and to receive energy from the inductively coupled primary circuit during the measurement phase, and wherein the resonant circuit comprises an inductor configured to be inductively coupled to the primary circuit and the first capacitor disposed in parallel with the inductor.

3. An apparatus according to claim 2 wherein the electrical energy store is disposed in parallel with the inductor during the transmission phase.

4. An apparatus according to claim 3 wherein respective capacitances of the first capacitor and the electrical energy store are equal.

5. An apparatus according to claim 2 wherein the resonant circuit is configured to receive energy from the inductively coupled primary circuit in accordance with a resonant frequency, and wherein the control signal is provided for a single period as defined by the resonant frequency prior to returning to the measurement phase.

6. An apparatus according to claim 1 wherein the estimate of the input that is based on the measured parameter is also based upon the threshold and a capacitance of the electrical energy store.

7. An apparatus according to claim 1 further comprising a sensor configured to measure the parameter and provide the input that is based on the measured parameter.

8. An apparatus according to claim 1 further comprising processing circuitry configured to determine the estimate of the input based upon a time between the transmission phases.

9. An apparatus comprising:
a primary circuit;
a secondary circuit inductively coupled to the primary circuit in order to receive energy from the primary circuit, wherein the secondary circuit comprises:
a resonant circuit configured to receive energy from the primary circuit during a series of measurement and transmission phases;
a sensor configured to provide an input based on a measured parameter during a measurement phase;
an electrical energy store configured to receive the input during the measurement phase;
comparison circuitry configured to compare a voltage that is based on the input that is received over time to a threshold; and
control circuit generation circuitry configured to provide a control signal at least partially in response to satisfaction of the threshold to trigger a transmission phase in which the voltage is discharged and a voltage of the primary circuit is correspondingly increased; and
a first switch associated with a first capacitor and a second switch associated with the electrical energy store, wherein the first switch and the second switch are responsive to the control signal so as to switchably replace the first capacitor with the electrical energy store during the transmission phase.

10. An apparatus according to claim 9 wherein the resonant circuit comprises an inductor configured to be inductively coupled to the primary circuit and the first capacitor disposed in parallel with the inductor.

11. An apparatus according to claim 10 wherein the electrical energy store is disposed in parallel with the inductor during the transmission phase.

12. An apparatus according to claim 9 further comprising processing circuitry configured to determine an estimate of the input based upon a time between the transmission phases, the threshold and a capacitance of the electrical energy store.

13. A method comprising:
providing a series of measurement and transmission phases, wherein:
during the measurement phase, the method further comprises:
receiving an input based on a measured parameter;
storing a voltage representative of the current received over time based on the input that has been received with a second capacitor;
comparing the voltage to a threshold;
triggering the transmission phase, and
during the transmission phase, the method further comprises:
providing a control signal to facilitate discharge of the voltage in response to satisfaction of the threshold by switchably replacing a first capacitor with the second capacitor; and
evaluating the transmission phases to determine an estimate of the input that is based on the measured parameter.

14. A method according to claim 13 further comprising:
inductively coupling to a primary circuit; and
receiving energy from the inductively coupled primary circuit during both the measurement and transmission phases.

15. A method according to claim 14 wherein receiving energy comprises receiving energy with a resonant circuit during the measurement phase, and wherein the resonant circuit comprises an inductor configured to be inductively coupled to the primary circuit and the first capacitor disposed in parallel with the inductor.

16. A method according to claim 15 the second capacitor is disposed in parallel with the inductor during the transmission phase.

17. A method according to claim 14 wherein the estimate of the input that is based on the measured parameter is also based upon the threshold and a capacitance of the second capacitor.

18. A method according to claim 14 wherein receiving energy from the inductively coupled primary circuit comprises receiving energy in accordance with a resonant frequency, and wherein the control signal is provided for a single period as defined by the resonant frequency prior to returning to the measurement phase.

19. A method according to claim 13 wherein receiving the input comprises receiving current representative of the measured parameter, and wherein the method further comprises:
- measuring the parameter with a sensor that provides the current representative of the measured parameter; and
- switchably disconnecting the sensor in response to the control signal to prevent receipt of the current representative of the measured parameter during the transmission phase.

20. A method according to claim 13 wherein evaluating the transmission phases to determine the estimate of the input comprises determining the estimate of the input based upon a time between the transmission phases.

* * * * *